United States Patent [19]
Okamoto et al.

[11] Patent Number: 5,130,537
[45] Date of Patent: Jul. 14, 1992

[54] PLASMA ANALYZER FOR TRACE ELEMENT ANALYSIS

[75] Inventors: Yukio Okamoto, Sagamihara; Takashi Iino, Katsuta; Satoshi Shimura, Kokubunji; Masamichi Tsukada, Minori; Hiromi Yamashita, Katsuta; Masatoshi Kitagawa, Mito, all of Japan

[73] Assignee: Hitachi, Ltd., Tokyo, Japan

[21] Appl. No.: 674,407

[22] Filed: Mar. 25, 1991

[30]  Foreign Application Priority Data

Mar. 30, 1990 [JP] Japan ................... 2-80943

[51] Int. Cl.$^5$ .............................................. H01J 49/12
[52] U.S. Cl. ..................... 250/281; 250/288
[58] Field of Search ................ 250/281, 288; 356/316; 219/121.51

[56]  References Cited
U.S. PATENT DOCUMENTS

| | | | |
|---|---|---|---|
| 3,943,363 | 3/1976 | Amblard | 250/288 |
| 4,902,099 | 2/1990 | Okamoto et al. | 250/281 |
| 4,948,962 | 8/1990 | Mitsui et al. | 250/288 |
| 4,963,735 | 10/1990 | Okamoto et al. | 250/288 |

FOREIGN PATENT DOCUMENTS 64-6351 1/1989 Japan .

Primary Examiner—Jack I. Berman
Assistant Examiner—James E. Beyer
Attorney, Agent, or Firm—Fay, Sharpe, Beall, Fagan, Minnich & McKee

[57]  ABSTRACT

A plasma analyzer for trace element analysis has a gas supply system comprising a plurality of gas sources, an electromagnetic valve provided on a line connecting each gas source to a plasma generating space, a buffer tank provided after the electromagnetic valve on the line, and a flow regulating flowmeter provided after the buffer tank on the line. Each electromagnetic valves is controlled for on-off operation and the corresponding buffer tank suppresses the sudden change of the flow rate of the corresponding gas, so that the composition of the gas supplied to the plasma generating space changes gradually in spite of the simple on-off operation of the electromagnetic valves. Thus, the fluctuation and extinction of the plasma attributable to the sudden change of the composition of the gas supplied to the plasma generating space can be effectively prevented.

10 Claims, 3 Drawing Sheets

PLASMA ANALYZER FOR TRACE ELEMENT ANALYSIS

BACKGROUND OF THE INVENTION

The present invention relates to a trace element analyzer employing a plasma, such as a plasma emission spectrometer or a plasma mass analyzer, and, more particularly, to an improved plasma analyzer for trace element analysis, capable of efficiently changing a gas supplied to a plasma and of efficiently mixing the gas in the plasma.

A representative example of a conventional plasma analyzer employing a plasma is disclosed, for example, in Japanese Patent Laid-open (Kokai) No. 64-6351. Shown in FIG. 4 are an argon (Ar) gas source 1a, a nitrogen ($N_2$) gas source 1b, first, second and third flow meters 2a, 2b and 2c eahc provided with a valve, fourth, fifth and sixth flowmeters 3a 3b and 3c each provided with a valve, a triple-tube plasma torch 4 having an outer chamber 4a, a middle chamber 4b and an inner chamber 4c, a coil 5, a plasma 6, a sample vessel 7, a nebulizer 8, a high frequency power source 9, a sampling cone 10, a skimmer 11, vacuum pumps 12a, 12b and 12c, a mass filter 13, a detector 14 and a signal processing unit 15.

The basic operation of this conventional plasma analyzer will be described hereinafter. In an initial state, the valves of the first to third flowmeters 2a to 2c are open respectively in openings allowing corresponding gases to flow at given flow rates, respectively, and the valves of the fourth to sixth flowmeters 3a to 3c are closed. In this state, Ar gas is supplied into the outer chamber 4a and the middle chamber 4b of the plasma torch 4 through the flowmeters 2a and 2b, respectively. A sample nebulized by the nebulizer 8 is carried by Ar gas supplied as a carrier gas through the flowmeter 2c into the inner chamber 4c of the plasma torch 4. The respective flow rates of the Ar gas supplied respectively into the outer chamber 4a, the middle chamber 4b and the inner chamber 4c are regulated by the valves of the flowmeters 2a, 2b and 2c, respectively. Then, the coil 5 is energized by high frequency power supplied by the high frequency power source 9 to generate the plasma 6 by the agency of a high frequency magnetic field created by the coil 5. Ions produced in the plasma are drawn through the sampling cone 10 and the skimmer 11 into a vacuum chamber, in which the ions are analyzed by the mass filter 13 and are detected by the detector 14. A detection signal provided by the detector 14 is sent to and processed by the signal processing unit 15 to obtain mass analysis data. The mass analysis data is used for drawing a mass spectrum by a recorder.

After thus generating the plasma by using Ar gas, the valves of the fourth to sixth flowmeters 3a to 3c are opened gradually to supply $N_2$ gas at given flow rates through the fourth to sixth flowmeters 3a to 3c into the outer chamber 4a, middle chamber 4b and inner chamber 4c of the plasma torch 4, so that Ar-$N_2$ mixed gases of different mixing ratios are supplied respectively into the outer chamber 4a and middle chamber 4b of the plasma torch 4, and an Ar-$N_2$ mixed gas serving as a carrier gas is supplied together with the nebulized sample nebulized by the nebulizer 8 into the inner chamber 4c of the plasma torch 4.

Then, the values of the flowmeters 2a to 2c are regulated to decrease the flow rates of the Ar gas gradually, monitoring the mass spectrum so that the peak of Ar and the peak of the objective element may not coincide with each other. If the respective peaks of Ar and the objective element coincide with each other, the valves of the flowmeters 3a to 3c are regulated so as to increase the flow rates of the $N_2$ gas so that the respective peaks of Ar and the objective element are separated from each other. Upon the separation of the respective peaks of Ar and the objective element, the gas compositions respectively in the outer chamber 4a, the middle chamber 4b and the inner chamber 4c are sustained.

Thus, the Ar gas mixed in the plasma is changed for $N_2$ gas to enable the measurement of the objective element without being disturbed by argon-related molecular ions.

Incidentally, it is possible that the plasma vanishes if the Ar gas is changed suddenly for $N_2$ gas in changing the gas mixed in the plasma. Therefore, the Ar gas must be changed gradually for $N_2$ gas to sustain the plasma. Nevertheless, the conventional plasma analyzer is not provided with satisfactory means for facilitate the gas changing operation and requires delicate operation for the adjustment of the valves of a plurality of flowmeters in combination with monitoring the mass spectrum, which requires much time and labor. Thus, the conventional plasma analyzer has problems in measuring efficiency and accessibility.

SUMMARY OF THE INVENTION

The present invention has been made to solve those problems in the conventional plasma analyzer, and it is therefore an object of the present invention to provide an improved plasma analyzer for trace element analysis, capable of enabling simple, efficient operation for changing the gas mixed in the plasma and for adjusting the composition of the gas.

In one aspect of the present invention, a plasma analyzer for trace element analysis is provided with a gas supply system for supplying gasses into a plasma, comprising a plurality of gas sources, solenoid valves connected respectively to the gas sources, buffer tanks respectively connected to the solenoid valves, and flow regulating flowmeters respectively connected to the buffer tanks.

Although the solenoid valves operate in an on-off mode to change the respective flow rates of the corresponding gases suddenly, the buffer takes suppress the sharp variation of gas flows so that the respective flows rates of the gases may change gradually. Accordingly, the composition of the gas supplied into the plasma changes gradually even if the flow of the component gases changes sharply due to the simple on-off operation of the solenoid valves, so that the extinction and fluctuation of the plasma due to the sudden change of the composition of the gas supplied into the plasma can be effectively prevented. Since troublesome flow rate adjusting operation including the delicate adjustment of the valves of a plurality of flowmeters is not necessary, the plasma analyzer of the present invention is readily accessible and is capable of efficiently carrying out operation for trace element analysis.

The above and other objects, features and advantages of the present invention will become more apparent from the following description taken in connection with the accompanying drawings.

DESCRIPTION OF THE PREFERRED EMBODIMENT

Figure 1:
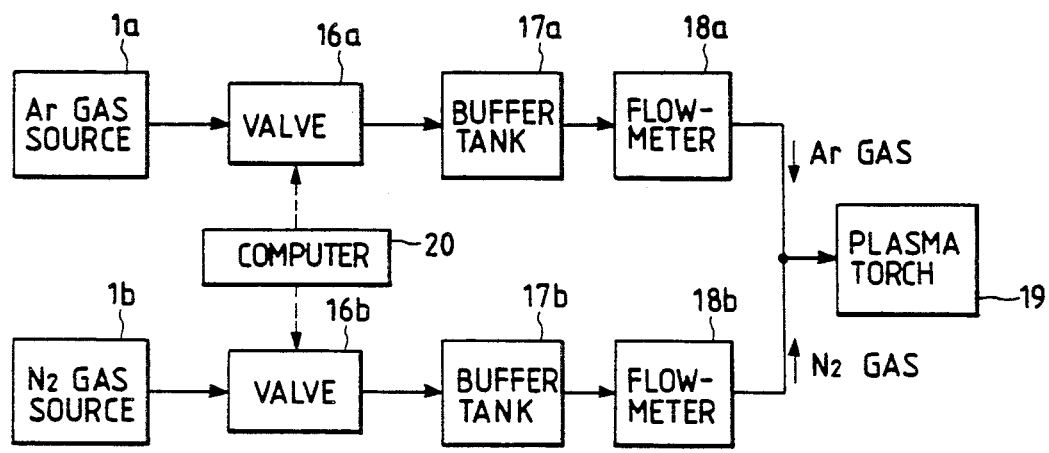
FIG. 1 is a block diagram of a gas supply system incorporated into a microwave-induced plasma analyzer for trace element analysis in a preferred embodiment according to the present invention.

Referring to FIG. 1 showing a gas supply stream incorporated into a plasma analyzer for trace element analysis in a preferred embodiment according to the present invention, an electromagnetic valve 16a and a buffer tank 17a (or a pipe of an equivalent volume) are provided on a line connecting a first flow regulating flowmeter 18a to a first gas source 1a, for example, an Ar gas cylinder, and an electromagnetic valve 16b and a buffer tank 17b (or a pipe of an equivalent volume) are provided on a line connecting a second flow regulating flowmeter 18b to a second gas source 1b, for example, a $N_2$ cylinder. The electromagnetic valves 16a and 16b are controlled by a computer 20. In FIG. 1, indicated at 19 is a plasma torch.

The buffer tanks 17a and 17b buffer sudden changes in the composition and pressure of a gas supplied to the plasma torch 19 due to the operation of the electromagnetic valves 16a and 16b in an on-off mode. Even if the electromagnetic valve 16a is closed instantaneously, the buffer tank 17a makes the flow rate of Ar gas supplied to the plasma torch 19 decrease gradually instead of immediately dropping to zero. On the other hand, even if the electromagnetic valve 16b is opened instantaneously, the buffer tank 17b makes the flow rate of $N_2$ gas increase gradually instead of sharply increasing to a maximum. Thus, the composition of the gas supplied to the plasma torch 19 changes gradually, so that the plasma does not fluctuate or does not extinct in changing the gas from Ar gas to $N_2$ gas. Similarly, the sudden change in the composition of the gas is prevented in changing the gas from $N_2$ gas to Ar gas. A time necessary for changing the composition of the gas can be determined selectively by selectively determining the respective capacities of the buffer tanks 17a and 17b.

Figure 2:
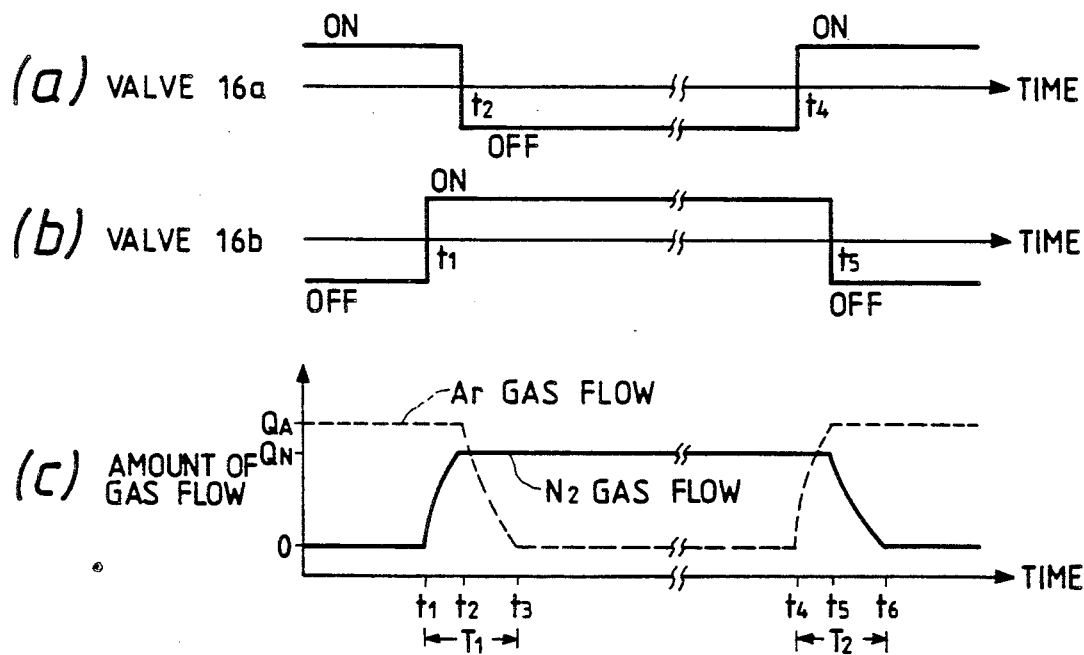
FIG. 2 (2a, 2b and 2c) is a time chart of assistance in explaining the basic actions of the gas supply system of FIG. 1.

This gas composition changing operation will be described with reference to a time chart shown in FIG. 2. In an initial state, the electromagnetic valve 16a is ON and the electromagnetic valve 16b is OFF as shown in FIGS. 2(a) and 2(b) to supply only Ar gas to the plasma torch 19 at a predetermined flow rate $Q_A$ (1 to 20 l/min) regulated by the flow regulating flowmeter 18a as shown in FIG. 2(c) and an Ar plasma is generated by the plasma torch 19. At time $t_1$, the electromagnetic valve 16b is turned ON to supply $N_2$ gas to the plasma torch 19 at a predetermined flow rate $Q_N$ (1 to 20 l/min) regulated by the flow regulating flowmeter 18b. The buffer tank 17b suppresses the instantaneous increase of the flow rate of $N_2$ gas flow zero to $Q_N$ at time $t_1$ so that the flow rate of $N_2$ gas increases gradually. After the flow rate of $N_2$ gas has arrived at the predetermined flow rate $Q_N$, the electromagnetic valve 16a is turned OFF at time $t_2$ to stop supplying Ar gas, and then the buffer tank 17a decreases the flow rate of Ar gas gradually. Consequently, the composition of the gas supplied to the plasma torch 19 changes gradually from an Ar-rich composition to a $N_2$-rich composition. At time $t_3$, the flow rate of Ar gas reaches zero and only $N_2$ gas is supplied to the plasma torch 19. Thus, the $N_2$ concentration of the gas supplied to the plasma torch 19 starts increasing from zero at time $t_1$, increases gradually between time $t_1$ and $t_2$, reaches 100% at time $t_3$, and only $N_2$ gas is supplied after time $t_3$. Thus, the plasma changes gradually from the Ar gas plasma to a $N_2$ gas plasma between time $t_1$ and time $t_3$.

The $N_2$ gas plasma is changed for the Ar gas plasma in the following manner. Before time $T_4$, the electromagnetic valve 16a is OFF and the electromagnetic valve 16b is ON to supply only $N_2$ gas to the plasma torch 19. At time $t_4$, the electromagnetic valve 16a is turned ON to start supplying Ar gas, and then the flow rate of Ar gas increases gradually. Upon the arrival of the flow rate of Ar gas at the predetermined flow rate $Q_A$ regulated by the flow regulating flowmeter 18a, the electromagnetic valve 16b is turned OFF at time $t_5$ and, consequently, the flow rate of $N_2$ gas decreases gradually to zero to time $t_6$, so that the plasma changed from the $N_2$ gas plasma to an Ar gas plasma.

The flow rate $Q_A$ of Ar gas in supplying only Ar gas to the plasma torch 19 and the flow rate $Q_N$ of $N_2$ gas in supplying only $N_2$ gas to the plasma torch 19 may be determined optionally by the flow regulating flowmeters 18a and 18b according to plasma generating conditons including the high frequency power, the microwave power and the configuration of the plasma torch 19. Generally, in changing over the plasma between an Ar gas plasma and a $N_2$ gas (or air) plasma, it is desirable that the flow rate $Q_A$ of Ar gas is in the range of 1 to 3 l/min, the flow rate $Q_N$ of $N_2$ gas is in the range of 8 to 10 l/min, and $Q_A < Q_N$, when, for example, the microwave power $W = 1$ kW and the plasma torch 19 has an inner tube having an inside diameter $d = 10$ mm.

A time $T_1$ and a time $T_2$ necessary for perfectly changing the plasma from an Ar gas plasma to a $N_2$ gas plasma, and from a $N_2$ gas plasma to an Ar gas plasma, respectively, can be optionally determined by adjusting the respective volumes of the buffer tanks 17a and 17b provided that other conditions are fixed. Usually, the times $T_1$ and $T_2$ are determined selectively in the range of 1 to 30 sec so that the plasma may not fluctuate or may not extinct.

Sequential control of the electromagnetic valves 16a and 16b by the computer 20 facilitates changing the gas supplied to the plasma torch 19.

Figure 3:
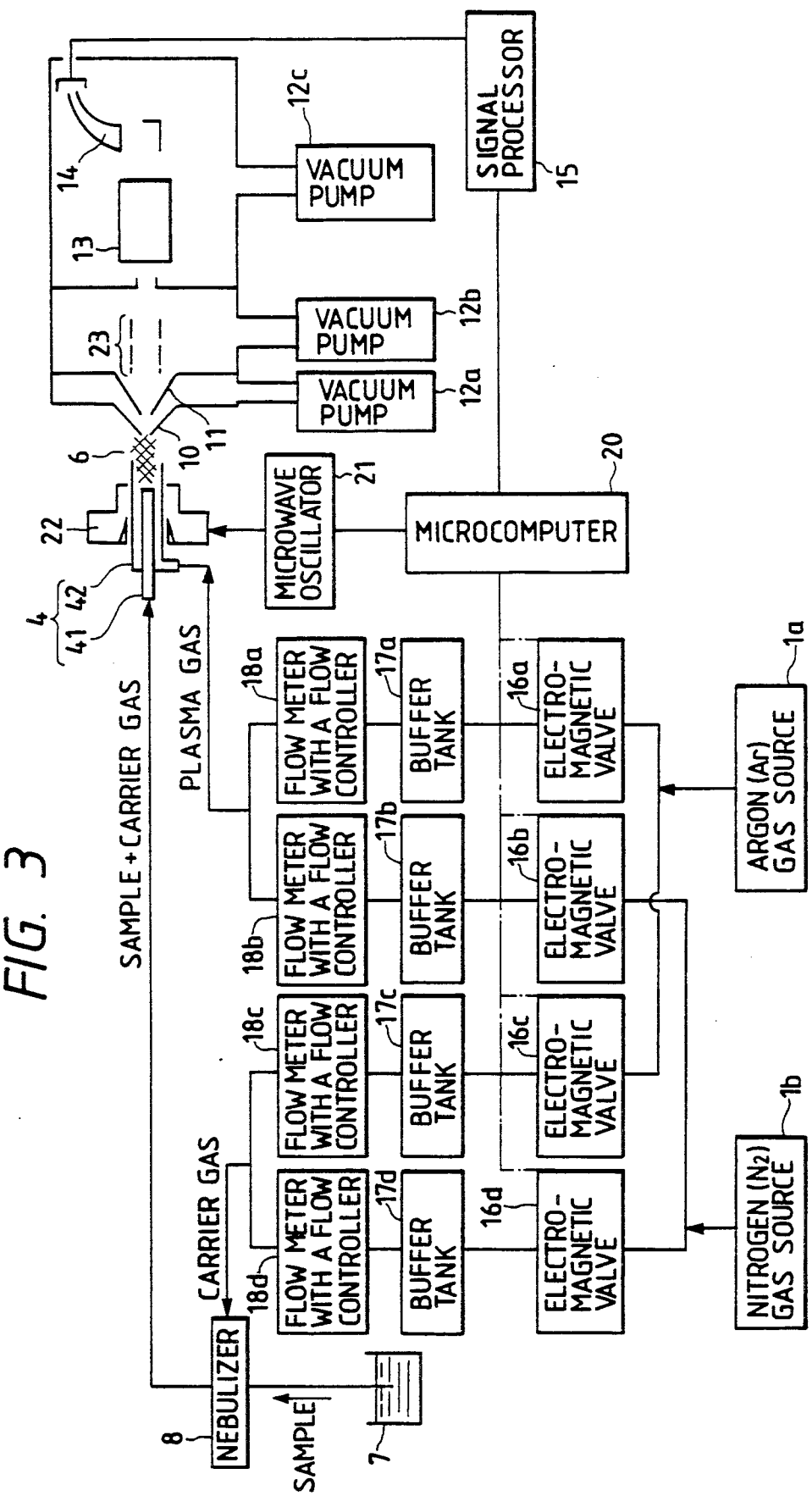
FIG. 3 is a block diagram of the microwave-induced plasma analyzer incorporating the gas supply system of FIG. 1.
Figure 4:
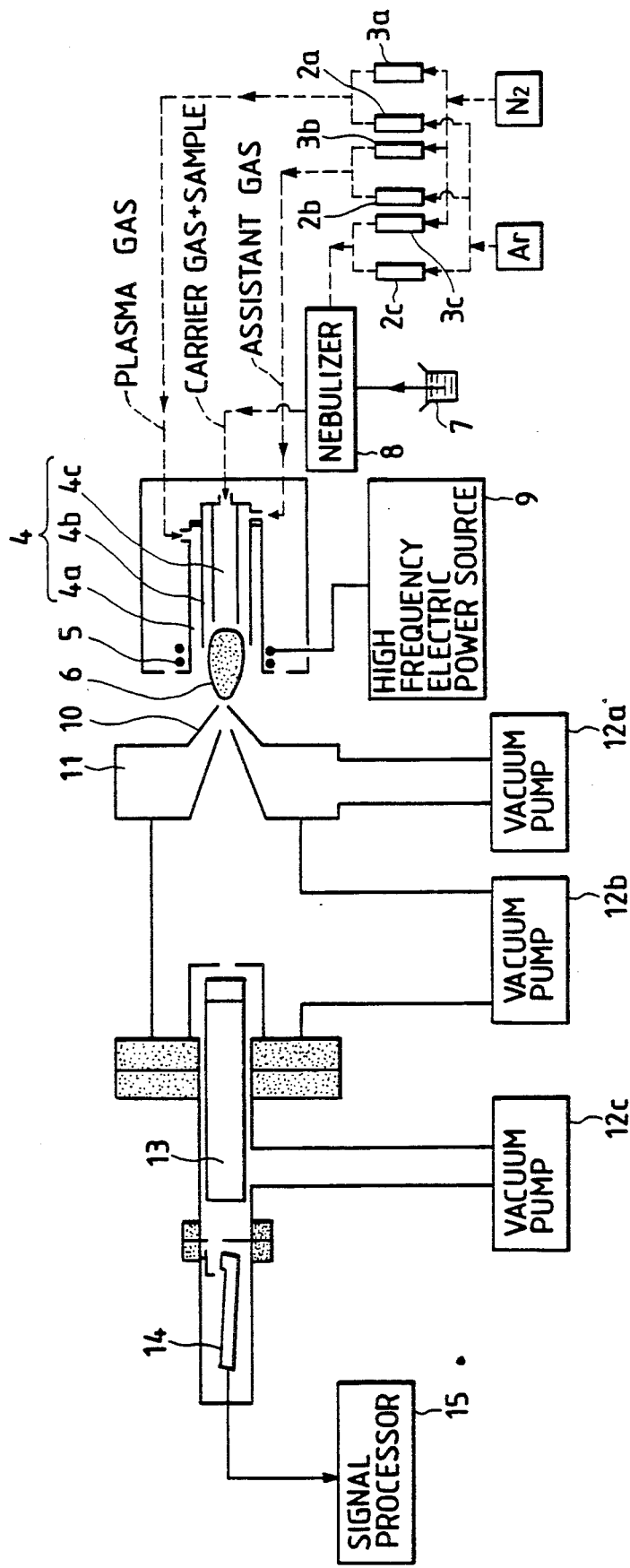
FIG. 4 is a diagrammatic view of a conventional plasma analyzer for trace element analysis.

Referring to FIG. 3 showing a plasma analyzer for trace element analysis in a preferred embodiment according to the present invention, there are shown an Ar gas source 1a, a $N_2$ gas source 1b, a plasma torch 4, electromagnetic valves 16a, 16b, 16c and 16d, buffer tanks 17a, 17b, 17c and 17d (or pipes of equivalent volumes), flow regulating flow meters 18a, 18b, 18c and 18d, microwave oscillator 21 for generating microwave power, a microwave cavity 22 of a surface wave type or a circularly polarized wave type through which microwave power is supplied to the plasma torch 4, and a microcomputer for controlling the electromagnetic valves 16a to 16d, the microwave oscillator 21 and a signal processor 15. The plasma torch 4 is of a double-tube construction having an inner tube 41 and an outer tube 42. A carrier gas and a sample is supplied into the inner tube 41, and a plasma is introduced into the annular space between the inner tube 41 and the outer tube 42.

The plasma analyzer operates in the following manner. all the electromagnetic valves 16a to 16d are OFF before the plasma analyzer is started. In starting the plasma analyzer, the electromagnetic valve 16a is turned ON to supply a plasma gas (Ar gas) through the buffer tank 17a and the flow regulating flowmeter 18a into the annular space between the inner tube 41 and outer tube 42 of the plasma torch 4, and the electromagnetic valve 16c is turned ON the supply a carrier gas (Ar gas) through the buffer tank 17c and the flow regulating flowmeter 18c to a nebulizer 8. A sample supplied from a sample vessel 7 to the nebulizer 8 is nebulized by the nebulizer 8 and is supplied together with the carrier gas into the inner tube 41 of the plasma torch 4. Subsequently, the microwave oscillator 21 is started to supply microwave power through the microwave cavity 22 to the plasma torch 4 to generate a plasma 6. Ions of the sample produced in the plasma 6 are drawn through a sampling cone 10 and a skimmer 11 into a vacuum chamber, are condensed by a lens system 23, are filtered by a mass filter 13 and are detected by a detector 14. The detector 14 gives a detection signal to the signal processor 15, which processes the detection signal to provide data for drawing a mass spectrum.

After the Ar gas plasma has been produced, the electromagnetic valve 16b is turned ON to mix $N_2$ gas supplied through the buffer tank 17b and the flow regulating flowmeter 18b in the plasma gas (Ar gas) in the space between the inner tube 41 and outer tube 42 of the plasma torch 4, and the electromagnetic valve 16d is turned ON to mix $N_2$ gas supplied through the buffer tank 17d and the flow regulating flowmeter 18d in the carrier gas (Ar gas) in the nebulizer 8. Although the electromagnetic valves 16b and 16d are turned ON suddenly, the buffer tanks 17b and 17b suppress the sharp increase in the flow rate of $N_2$ gas to increase the the same gradually as shown in FIG. 3.

Upon the increase of the flow rate of $N_2$ gas supplied to the plasma torch 4 and that of $N_2$ gas supplied to the nebulizer 8 to predetermined flow rates regulated by the flow regulating flowmeters 18b and 18d, respectively, the electromagnetic valves 16a and 16b are turned OFF to stop supplying Ar gas, in which the buffer tank 17a and 17c suppress the sharp decrease in the flow rates of Ar gas so that the flow rates decreases gradually as shown in FIG. 3. Eventually, only $N_2$ gas is supplied as the plasma gas and the carrier gas.

Since the plasma gas and the carrier gas are changed gradually from Ar gas to $N_2$ gas, the plasma neither fluctuates nor extincts during the change of Ar gas for $N_2$ gas, and the measurement of objective elements is achieved stably and accurately without being disturbed by argon-related molecular ions.

In changing the plasma gas and the carrier gas from $N_2$ gas to Ar gas, the electromagnetic valves 16b and 16d are turned OFF a short time after the electromagnetic valves 16a and 16c have been turned ON.

All the foregoing operations are controlled according to a sequentially control program by the microcomputer 20. The carrier gas (Ar gas) may be supplied to the plasma torch 4 after generating an Ar plasma in the plasma torch 4 or the plasma gas (Ar gas) and the carrier gas (Ar gas) may be supplied simultaneously to the plasma torch 4. In changing the gases supplied to the plasma torch 4, the timing of operating the electromagnetic valve 16a of the plasma gas supply system and that of operating the electromagnetic valve 16c of the carrier gas supply system need not necessarily coincide with each other; there may be a time lag between the operation of the electromagnetic valve 16a and that of the electromagnetic valve 16c. The same timing mode applies to the timing of operating the electromagnetic valve 16b and that of operating the electromagnetic valve 16d. Although the timing of turning OFF the electromagnetic valve 16a is delayed relative to the timing of turning ON the electromagnetic valve 16b in changing the Ar gas for $N_2$ gas, and the timing of turning OFF the electromagnetic valve 16b is delayed relative to the timing of turning ON the electromagnetic valve 16a in changing $N_2$ gas for Ar gas in the exemplary mode of operation of the plasma analyzer as described above with reference to FIG. 2, the electromagnetic valves 16a and 16b may be operated simultaneously.

Although the manner of changing the plasma gas and the carrier gas between Ar gas and $N_2$ gas has been described, the gases to be used by the present invention are not limited to Ar gas and $N_2$ gas. When a gas which is more difficult to generate a plasma than Ar gas, such as helium gas (He gas), oxygen gas ($O_2$ gas) or air, is used, Ar gas is supplied first to produce an Ar plasma, and then Ar gas may be changed for He gas, $O_2$ gas or air. The gas supplied to the plasma torch 4 need not necessarily be changed from pure Ar gas through a Ar-$N_2$ mixed gas to pure $N_2$ gas; the gas may be, for example, a gas of 5% Ar and 95% $N_2$.

Means for generating the plasma is not limited only to microwave power; high frequency power or dc power may be used for generating the plasma.

As is apparent from the foregoing description, according to the present invention, the composition of the gas supplied into the plasma can be efficiently changed, and the plasma analyzer for trace element analysis is accessible. Since the plasma analyzer of the present invention is capable of readily generating a plasma of a gas difficult to produce a plasma under the atmospheric pressure, such as $N_2$ gas, He gas on air, inexpensive $N_2$ gas on air may be used instead of expensive Ar gas. Furthermore, the trace elements contained in the sample can be accurately analyzed, because the highly accurate separation and detection of disturbed ions, i.e., ions of the same mass, disturbed by the gas of the plasma is possible.

What is claimed is:

1. A plasma analyzer for trace element analysis, comprising:
   plasma generating means for generating a plasma in a plasma generating space;
   plasma gas supply means for supplying a plasma gas into the plasms generating space;
   sample supply means for introducing an assay sample into the plasma generating space; and
   detecting means for detecting the component elements of the assay sample excited in the plasma generated in the plasma generating space;
   wherein said plasma gas supply means comprises:
   a first gas source for supplying a first gas,
   a second gas source for supplying a second gas,
   a first valve for allowing the first gas to flow from the first gas source to the plasma generating space and for intercepting the flow of the first gas to the plasma generating space, a second valve for allowing the second gas to flow from the second gas source to the plasma generating space and for intercepting the flow of the second gas to the plasma generating space, a first buffer tank provided after the first valve on a line connecting the first gas source to the plasma generating space, a second buffer tank provided after the second valve on a line connecting the second gas source to the plasma generating space, a first flow regulating flowmeter provided after the first buffer tank on the line connecting the first gas source to the plasma generating space, a second flow regulating flowmeter provided after the second buffer tank on the line connecting the second gas source to the plasma generating space, and a piping system for supplying the first and second gases from the first and second gas sources through the first and second flow regulating flowmeters, respectively, into the plasma generating space.

2. A plasma analyzer for trace element analysis according to claim 1, wherein said first and second valves are electromagnetic valves.

3. a plasma analyzer for trace element analysis according to claim 1, wherein said first and second valves are controlled according to a sequentially control program by control means.

4. A plasma analyzer for trace element analysis according to claim 1, wherein said first gas is argon gas, and said second gas is nitrogen gas.

5. A plasma analyzer for trace element analysis according to claim 1, wherein said first gas is argon gas, and said second gas is a mixture of argon gas and nitrogen gas.

6. A plasma analyzer for trace element analysis according to claim 1, wherein said first gas is argon gas, and said second gas is helium gas.

7. A plasma analyzer for tracer element analysis according to claim 1, wherein said first gas is argon, and said second gas is oxygen gas.

8. A plasma analyzer for trace element analysis according to claim 1, wherein said first gas is argon gas, and said second gas is air.

9. A plasma analyzer for trace element analysis according to claim 1, wherein said plasma generating means employs microwave power for generating a plasma.

10. A plasma analyzer for trace element analysis according to claim 1, wherein said detecting means detects the ions of the components of the sample produced in the plasma by separating the ions according to their masses.

* * * * *